(12) United States Patent  (10) Patent No.: US 7,632,970 B2
Takemoto  (45) Date of Patent: Dec. 15, 2009

(54) ASYMMETRIC UREA COMPOUND AND PROCESS FOR PRODUCING ASYMMETRIC COMPOUND BY ASYMMETRIC CONJUGATE ADDITION REACTION WITH THE SAME AS CATALYST

(75) Inventor: Yoshiji Takemoto, Otsu (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 466 days.

(21) Appl. No.: 10/562,579

(22) PCT Filed: Jun. 25, 2004

(86) PCT No.: PCT/JP2004/009350

§ 371 (c)(1),
(2), (4) Date: Dec. 27, 2005

(87) PCT Pub. No.: WO2005/000803

PCT Pub. Date: Jan. 6, 2005

(65) Prior Publication Data

US 2006/0161006 A1  Jul. 20, 2006

(30) Foreign Application Priority Data

Jun. 30, 2003 (JP) ............................. 2003-189096
Dec. 18, 2003 (JP) ............................. 2003-421688

(51) Int. Cl.
  *C07C 275/00* (2006.01)
(52) U.S. Cl. .................. 564/63; 564/3; 564/17; 564/26; 564/29
(58) Field of Classification Search .................. 564/3, 564/17, 26, 29, 63
See application file for complete search history.

(56) References Cited

U.S. PATENT DOCUMENTS

2003/0229121 A1  12/2003  Du Bois et al.

FOREIGN PATENT DOCUMENTS

| EP | 0 903 349 A2 | * | 3/1999 |
|---|---|---|---|
| JP | 2005516947 A | | 6/2005 |
| JP | 2005533038 A | | 11/2005 |
| JP | 2007502311 A | | 2/2007 |
| WO | WO 03/022799 A | | 3/2003 |
| WO | WO 03/045393 A | | 6/2003 |
| WO | WO 03/045917 A2 | | 6/2003 |
| WO | WO 03/045937 A1 | * | 6/2003 |
| WO | 03053434 A1 | | 7/2003 |
| WO | 03101984 A1 | | 12/2003 |
| WO | 2004103976 A2 | | 12/2004 |
| WO | WO 2005/058805 A1 | | 6/2005 |

OTHER PUBLICATIONS

Y. Takemoto et al., "Enantioselective Michael Reaction of Malonates to Nitroolefines Catalyzed by Bifunctional Organocatalysts", *Journal of the American Chemical Society*, vol. 125, No. 42, 2003, pp. 12672-12673.

M. L. Tommasino et al., "Asymmetric hydrogenation of enamides with catalysts containing chiral thiourea ligands", *Tetrahedron Asymmetry*, vol. 11, No. 24, 2000, pp. 4835-4841.

(Continued)

*Primary Examiner*—Peter G O'Sullivan
*Assistant Examiner*—Sudhakar Katakam
(74) *Attorney, Agent, or Firm*—Sughrue Mion, PLLC

(57) ABSTRACT

The present invention relates to a production method of asymmetric compound (IV) which includes conjugately adding nucleophilic reagent (III) to compound (II) in the presence of asymmetric urea compound (I). The present invention provides a non-metallic asymmetric catalyst capable of realizing a highly stereoselective asymmetric conjugate addition reaction in a high yield, and an advantageous production method of an asymmetric compound by an asymmetric conjugate addition reaction using the asymmetric catalyst.

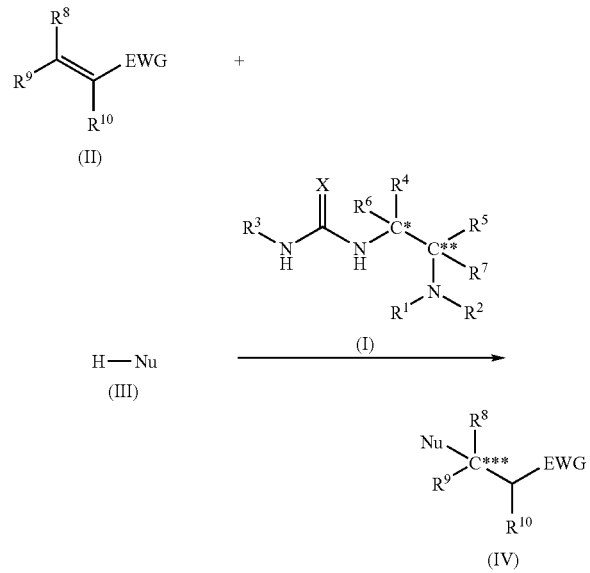

wherein X is an oxygen atom or a sulfur atom; $C^*$, $C^{}$ and $C^{*}$ are asymmetric carbons; $R^1$, $R^2$, $R^4$, $R^5$, $R^8$, $R^9$ and $R^{10}$ are each a lower alkyl group optionally having substituent(s) and the like, or $R^4$ and $R^5$ and the like in combination optionally form a homocyclic ring optionally having substituent(s) and the like; $R^3$ is an aryl group optionally having substituent (s) and the like; $R^6$ and $R^7$ are each a hydrogen atom and the like; Nu is —$CR^{16}(COR^{17})(COR^{18})$ wherein $R^{16}$, $R^{17}$ and $R^{18}$ are each a lower alkyl group optionally having substituent (s) and the like, and the like; and EWG is an electron withdrawing group.

7 Claims, No Drawings

OTHER PUBLICATIONS

U.S. Appl. No. 11/341,852, to Takemoto et al., filed Jan. 30, 2006.

T. Okino et al., "Enantio- and Diastereoselective Michael Reaction of 1,3-Dicarbonyl Compounds to Nitroolefins Catalyzed by a Bifunctional Thiourea", J. Am. Chem. Soc. 2005, vol. 127, No. 1, pp. 119-125.

Y. Hoashi et al., "Enantioselective Michael Addition to α,β- Unsaturated Imides Catalyzed by a Bifunctional Organocatalyst", Angew. Chem. Int. Ed., 2005, 44, pp. 4032-4035.

Y. Hoashi et al., "Bifunctional thiourea-catalyzed enantioselective double Michael reaction of γδ-unsaturated β-ketoester to nitroalkene: asymmetric synthesis of (-)-epibatidine", Tetrahedron Letters 45, (2004), pp. 9185-9188.

De Costa, B.R. et al., "A Practical Synthesis, Optical Resolution and Determination of Absolute Configuration of Enantiomerically Pure 1S,2R-(+)- and 1R,2S-(-)-CIS-2-(1-Pyrrolikinyl)Cyclohexyl Amines: Important Precursors for a new class of Sigma-Receptor Ligands and Anticonvulsant Drugs", Heterocycles, vol. 31, No. 10, (1990), pp. 1837-1846.

Pandy, B.R. et al., "Interrelationship between anticonvulsant and enzyme inhibitory properties of N-methyl-N-2-[1-(1-arylthiocarbamido)]cyclopentyl nitrobenzamides", Pharmacological Research Communications, vol. 13, No. 1, (1981), pp. 65-74.

Southwick, P.L. et al., "The Stereochemistry of Conjugate Additions. A Study of the Addition of Amines to (2-Nitropropenyl)-Benzene", Journal of the American Chemical Society, vol. 79, (1957), pp. 6222-6229.

Barnes, D.M. et al., "Development of a Catalytic Enantioselective Conjugate Addition of 1, 3-Dicarbonyl Compounds to Nitroalkenes for the Synthesis of Endothelin-A Antagonist ABT-546. Scope, Mechanism, and Further Application to the Synthesis of the Antidepressant Rolipram", Journal of the American Chemical Society, vol. 122, No. 44, (2002), pp. 13097-13105.

Ji, J. et al, "Catalytic Enantioselective Conjugate Addition of 1, 3-Dicarbonyl Compounds to Nitroalkenes", Journal of the American Chemical Society, vol. 121, No. 43, (1999), pp. 10215-10216.

Toshio Isobe et al., Modified Guanidines as Potential Chiral Superbases.2. Preparation of 1,3-Unsubstituted and 1-Substituted 2-Iminoimidazolidine Derivatives and a Related Guanidine by the 2-Chloro-1,3-dimethylimidazolinium Chloride-Induced Cyclization of Thioureas, J. Org. Chem. 2000, 65, pp. 7774-7778.

Catherine Bied et al., Chiral amino-urea derivatives of (1R, 2R)-1,2-diaminocyclohexane as ligands in the ruthenium catalysed asymmetric reduction of aromatic ketones by hydride transfer, Tetrahedron: Asymmetry 12 (2001) pp. 329-336.

* cited by examiner

ASYMMETRIC UREA COMPOUND AND PROCESS FOR PRODUCING ASYMMETRIC COMPOUND BY ASYMMETRIC CONJUGATE ADDITION REACTION WITH THE SAME AS CATALYST

TECHNICAL FIELD

The present invention relates to a novel asymmetric urea compound useful as a catalyst for asymmetric synthesis. Moreover, the present invention relates to a production method of asymmetric compounds, which comprises an asymmetric conjugate addition reaction using the asymmetric urea compound as a catalyst.

BACKGROUND ART

Asymmetric compounds obtained by asymmetric conjugate addition reaction to electron-deficient olefin such as nitroolefin compound, α,β-unsaturated carbonyl compound and the like are useful as intermediates for synthesizing amines, amino acids, pharmaceutical agents, agricultural chemicals, food additives and the like (e.g., Journal of the American Chemical Society, vol. 124, No. 44, p. 13097-13105 (2002)), and various production methods have been reported so far.

However, many of them require a stoichiometric amount of an asymmetric reagent (Journal of the American Chemical Society, vol. 124, No. 39, p. 11689-11698 (2002)), and most of the catalytic asymmetric conjugate addition reactions require strict reaction conditions or involve use of a metal catalyst (Tetrahedron, vol. 58, No. 29, p. 5773-5778 (2002)) and Synlett, special edition, p. 879-887 (2001)), which cause inefficient cost and operation, as well as environmental problems.

As a catalytic asymmetric conjugate addition reaction without using a metal catalyst, a Michael reaction to a nitroolefin compound using L-proline as a catalyst has been reported (Synlett, vol. 1, p. 26-28 (2002)). However, its stereoselectivity was unsatisfactorily low.

Furthermore, a Michael reaction to a nitroolefin compound using an asymmetric catalyst consisting of a magnesium salt and an asymmetric ligand has been reported (Journal of the American Chemical Society, vol. 121, No. 43, p. 10215-10216 (1999)). This method achieved high stereoselectivity, but is associated with limitations because it cannot be applied to bulky nucleophilic reagents having tertiary carbon etc., and the like.

DISCLOSURE OF THE INVENTION

The present invention has been made to solve the above-mentioned problems found in the conventional asymmetric conjugate addition reactions and aims at providing a non-metallic asymmetric catalyst capable of achieving a highly stereoselective asymmetric conjugate addition reaction in a high yield, and a production method of an asymmetric compound useful as an intermediate for synthesizing amines, amino acids, pharmaceutical agents, agricultural chemicals, food additives and the like, which is more advantageous than conventional methods, by developing an asymmetric conjugate addition reaction using the asymmetric catalyst.

To solve the above-mentioned problems, the present inventors took note of a compound wherein both of an acidic moiety that activates an electron-deficient olefin and a basic moiety that activates a nucleophilic reagent are bonded to optically active scaffolds, as a non-metallic asymmetric catalyst for a conjugate addition reaction, and conducted intensive studies. Consequently, they found a novel asymmetric urea compound, which resulted in the completion of the present invention.

Accordingly, the present invention provides the following.

(1) A compound represented by the formula (I):

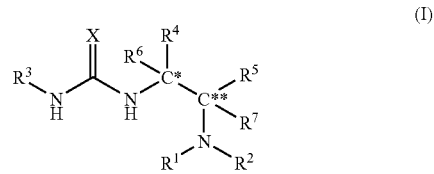

wherein

X is an oxygen atom or a sulfur atom;

C* and C** are each independently an asymmetric carbon;

$R^1$ and $R^2$ are
  the same or different and each is a lower alkyl group optionally having substituent(s), an aralkyl group optionally having substituent(s) or an aryl group optionally having substituent(s), or $R^1$ and $R^2$ optionally form, together with the nitrogen atom they are bonded to, an aliphatic heterocycle optionally having substituent(s) (the aliphatic heterocycle is optionally condensed with an aromatic hydrocarbon);

$R^3$ is
  a lower alkyl group optionally having substituent(s), an aralkyl group optionally having substituent(s), an aryl group optionally having substituent(s) or a heteroaryl group optionally having substituent(s);

$R^4$ and $R^5$ are
  the same or different and each is a lower alkyl group optionally having substituent(s), an aralkyl group optionally having substituent(s) or an aryl group optionally having substituent(s), or $R^4$ and $R^5$ optionally form, together with the asymmetric carbons they are respectively bonded to, a homocyclic ring optionally having substituent(s) or a heterocycle optionally having substituent(s); and $R^6$ and $R^7$ are
  the same or different and each is a hydrogen atom or a lower alkyl group optionally having substituent(s),

[hereinafter also referred to as asymmetric urea compound (I)], or a salt thereof.

(2) The asymmetric urea compound (I) of the above-mentioned (1), wherein X is a sulfur atom, or a salt thereof.

(3) The asymmetric urea compound (I) of the above-mentioned (1) or (2), wherein $R^4$ and $R^5$ form, together with the asymmetric carbons they are respectively bonded to, cyclopropane, cyclobutane, cyclopentane or cyclohexane, or a salt thereof.

(4) The asymmetric urea compound (I) of the above-mentioned (3), wherein $R^4$ and $R^5$ form cyclohexane together with the asymmetric carbons they are respectively bonded to, and $R^6$ and $R^7$ are each a hydrogen atom, or a salt thereof.

(5) The asymmetric urea compound (I) of the above-mentioned (4), wherein the absolute configurations of C* and C** are both S-configurations or both R-configurations, or a salt thereof.

(6) A method of producing a compound represented by the formula (IV):

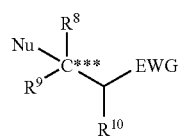

wherein

C*** is an asymmetric carbon;

$R^8$, $R^9$ and $R^{10}$ are the same or different and each is a hydrogen atom, a lower alkyl group optionally having substituent(s), an aralkyl group optionally having substituent(s), an aryl group optionally having substituent(s), a heteroaryl group optionally having substituent(s), a hetero atom optionally having substituent(s) or an electron withdrawing group, or $R^9$ and $R^{10}$ optionally form, together with the carbon atoms they are respectively bonded to, a homocyclic ring optionally having substituent(s) or a heterocycle optionally having substituent(s), provided that $R^8$ and $R^9$ are not the same groups;

EWG is an electron withdrawing group selected from a nitro group, a cyano group, $-COR^{11}$, $-SO_2R^{12}$, $-COOR^{13}$ and $-PO(OR^{14})(OR^{15})$ wherein $R^{11}$, $R^{12}$, $R^{13}$, $R^{14}$ and $R^{15}$ are the same or different and each is a hydrogen atom, a lower alkyl group optionally having substituent(s), an aralkyl group optionally having substituent(s), an aryl group optionally having substituent(s) or a heteroaryl group optionally having substituent(s), or $R^{11}$ and $R^8$, or $R^{11}$ and $R^{10}$, optionally form, together with the carbon atom(s) they are respectively bonded to, a homocyclic ring having an electron withdrawing group and optionally having substituent(s); and Nu is $-CR^{16}(COR^{17})(COR^{18})$, $-OR^{19}$, $-SR^{20}$, $-NR^{21}R^{22}$, $-C(NO)R^{23}R^{24}$ wherein $R^{16}$ is a hydrogen atom, a halogen atom, a hetero atom having substituent(s), a lower alkyl group optionally having substituent(s) or an aryl group optionally having substituent(s);

$R^{17}$ and $R^{18}$ are the same or different and each is a hydrogen atom, a lower alkyl group, a lower alkoxy group, a mono-lower alkylamino group or a di-lower alkylamino group;

$R^{16}$ and $R^{17}$ optionally form, together with the carbon atoms they are respectively bonded to, a homocyclic ring optionally having substituent(s) or a heterocycle optionally having substituent(s) (the homocyclic ring and heterocycle are optionally condensed with an aromatic hydrocarbon); and $R^{19}$, $R^{20}$, $R^{21}$, $R^{22}$, $R^{23}$ and $R^{24}$ are the same or different and each is a hydrogen atom, a lower alkyl group optionally having substituent(s), an aralkyl group optionally having substituent(s), an aryl group optionally having substituent(s) or a heteroaryl group optionally having substituent(s), or $R^{21}$ and $R^{22}$ optionally form, together with the nitrogen atom they are bonded to, an aliphatic heterocycle optionally having substituent(s), or an azido group,

[hereinafter to be also referred to as asymmetric compound (IV)], or a salt thereof, which comprises conjugately adding a nucleophilic reagent represented by the formula (III): H-Nu (III) wherein Nu is as defined above, [hereinafter to be also referred to as nucleophilic reagent (III)], to a compound represented by the formula (II):

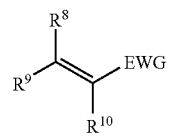

wherein each symbol is as defined above, [hereinafter to be also referred to as compound (II)], or a salt thereof, in the presence of asymmetric urea compound (I) of any of the above-mentioned (1) to (5) or a salt thereof.

(7) The method of the above-mentioned (6), wherein Nu is $-CR^{16}(COR^{17})(COR^{18})$, $-OR^{19}$, $-SR^{20}$, $-NR^{21}R^{22}$, $-C(NO_2)R^{23}R^{24}$ wherein $R^{16}$ is a hydrogen atom, a halogen atom, a lower alkyl group optionally having substituent(s) or an aryl group optionally having substituent(s);

$R^{17}$ and $R^{18}$ are the same or different and each is a hydrogen atom, a lower alkyl group, a lower alkoxy group, a mono-lower alkylamino group or a di-lower alkylamino group;

$R^{19}$, $R^{20}$, $R^{21}$, $R^{22}$, $R^{23}$ and $R^{24}$ are the same or different and each is a hydrogen atom, a lower alkyl group optionally having substituent(s), an aralkyl group optionally having substituent(s), an aryl group optionally having substituent(s) or a heteroaryl group optionally having substituent(s), or $R^{21}$ and $R^{22}$ optionally form, together with the nitrogen atom they are bonded to, an aliphatic heterocycle optionally having substituent(s), or an azido group.

(8) The method of the above-mentioned (6) or (7), wherein the electron withdrawing group for EWG is a nitro group.

(9) The method of any of the above-mentioned (6) to (8), wherein $R^8$ and $R^{10}$ are each a hydrogen atom, and $R^9$ is a lower alkyl group optionally having substituent(s), an aryl group optionally having substituent(s) or a heteroaryl group optionally having substituent(s).

(10) The method of any of the above-mentioned (6) to (9), wherein the nucleophilic reagent (III) is represented by $HCR^{16}(COR^{17})(COR^{18})$ wherein each symbol is as defined above.

(11) The method of the above-mentioned (10), wherein $R^{16}$ is a hydrogen atom, a lower alkyl group optionally having substituent(s), a halogen atom or a hetero atom having substituent(s), and $R^{17}$ and $R^{18}$ are the same or different and each is a lower alkoxy group.

(12) The method of the above-mentioned (11), wherein $R^{16}$ is a hydrogen atom, methyl, a chlorine atom, methoxy or tert-butoxycarbonylamino, and $R^{17}$ and $R^{18}$ are each methoxy or ethoxy.

(13) The method of the above-mentioned (10), wherein $R^{16}$ and $R^{17}$ optionally form, together with the carbon atoms they are respectively bonded to, a homocyclic ring optionally having substituent(s) (the homocyclic ring is optionally condensed with an aromatic hydrocarbon).

(14) The method of the above-mentioned (13), wherein the homocyclic ring is 1,2,3,4-tetrahydronaphthalen-1-one.

(15) The method of any of the above-mentioned (6) to (14), which is performed in at least one solvent selected from toluene and methylene chloride.

(16) The method of any of the above-mentioned (6) to (14), which is performed without a solvent.

DETAILED DESCRIPTION OF THE INVENTION

The present invention is described in detail in the following.

First, each symbol used in the present description is defined in the following.

The alkyl used in the present invention is linear when it is free of a prefix (e.g., iso, neo, sec-, tert- and the like). For example, a simple propyl means linear propyl.

The "halogen atom" for $R^{16}$ is fluorine atom, chlorine atom, bromine atom or iodine atom, and preferred are chlorine atom and bromine atom.

The "lower alkyl group" for $R^{17}$ or $R^{18}$ is a straight chain or branched chain alkyl group having 1 to 12 carbon atoms, and, for example, methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl and the like can be mentioned. Preferred are methyl, ethyl and propyl.

The "lower alkoxy group" for $R^{17}$ or $R^{18}$ is an alkoxy group wherein the alkyl moiety is the "lower alkyl group" defined above, and, for example, methoxy, ethoxy, propoxy, isopropoxy, butoxy, isobutoxy, sec-butoxy, tert-butoxy, pentoxy, isopentoxy, neopentoxy, hexyloxy, heptyloxy, octyloxy, nonyloxy, decyloxy, undecyloxy, dodecyloxy and the like can be mentioned. Preferred are methoxy and ethoxy.

The "mono-lower alkylamino group" for $R^{17}$ or $R^{18}$ is a mono-alkylamino group wherein the alkyl moiety is the "lower alkyl group" defined above, and, for example, N-methylamino, N-ethylamino, N-propylamino, N-isopropylamino, N-butylamino, N-isobutylamino, N-sec-butylamino, N-tert-butylamino, N-pentylamino, N-isopentylamino, N-neopentylamino, N-hexylamino, N-heptylamino, N-octylamino, N-nonylamino, N-decylamino, N-undecylamino, N-dodecylamino and the like can be mentioned.

The "di-lower alkylamino group" for $R^{17}$ or $R^{18}$ is a di-alkylamino group wherein the alkyl moieties are the same or different and each is the "lower alkyl group" defined above, and, for example, N,N-dimethylamino, N,N-diethylamino, N,N-dipropylamino, N,N-diisopropylamino, N,N-dibutylamino, N,N-diisobutylamino, N,N-di-sec-butylamino, N,N-di-tert-butylamino, N,N-dipentylamino, N,N-diisopentylamino, N,N-dineopentylamino, N,N-dihexylamino, N,N-diheptylamino, N-methyl-N-ethylamino, N-methyl-N-propylamino, N-methyl-N-isopropylamino, N-methyl-N-butylamino, N-methyl-N-isobutylamino, N-methyl-N-sec-butylamino, N-methyl-N-tert-butylamino, N-methyl-N-pentylamino, N-methyl-N-isopentylamino, N-methyl-N-neopentylamino, N-methyl-N-hexylamino, N-methyl-N-heptylamino, N-methyl-N-octylamino, N-methyl-N-nonylamino, N-methyl-N-decylamino, N-methyl-N-undecylamino, N-methyl-N-dodecylamino and the like can be mentioned.

As the "lower alkyl group" of the "lower alkyl group optionally having substituent(s)" for $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ or $R^{24}$, alkyl groups same as the "lower alkyl group" defined above can be mentioned.

The lower alkyl group optionally has substituent(s) at substitutable position(s), and as such substituent(s), a lower alkoxy group (exemplified by those defined above), a mono-lower alkylamino group (exemplified by those defined above), a di-lower alkylamino group (exemplified by those defined above), a halogen atom (exemplified by those defined above), a nitro group, a cyano group, —$COOR^{25}$ wherein $R^{25}$ is a lower alkyl group as defined above, and the like can be mentioned. The number of substituents is not particularly limited, but is preferably 1 to 3. When it is 2 or more, the substituents may be the same or different.

The "aryl group" of the "aryl group optionally having substituent(s)" for $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{19}$, $R^{20}$, $R^{21}$, $R^{22}$, $R^{23}$ or $R^{24}$ is an aryl group having 6 to 20 carbon atoms, and, for example, phenyl, 1- or 2-naphthyl, biphenyl, binaphthyl and the like can be mentioned.

The aryl group optionally has substituent(s) at substitutable position(s), and as such substituent(s), a lower alkyl group (exemplified by those defined above), a lower alkoxy group (exemplified by those defined above), a mono-lower alkylamino group (exemplified by those defined above), a di-lower alkylamino group (exemplified by those defined above), a halogen atom (exemplified by those defined above), a haloalkyl group (lower alkyl group substituted by one or more halogen atoms, such as trifluoromethyl etc.), a nitro group, a cyano group, —$COOR^{25}$ wherein $R^{25}$ is as defined above, and the like can be mentioned. The number of substituents is not particularly limited, but is preferably 1 to 3. When it is 2 or more, the substituents may be the same or different.

The "substituent" of the "aryl group optionally having substituent(s)" for $R^3$ is preferably an alkyl group, a haloalkyl group, a nitro group, a cyano group, —$COOR^{25}$ wherein $R^{25}$ is as defined above, and the like, more preferably a haloalkyl group and the like.

The "aralkyl group" of the "aralkyl group optionally having substituent(s)" for $R^1$, $R^2$, $R^3$, $R^4$, $R^5$, $R^8$, $R^9$, $R^{10}$, $R^{11}$, $R^{12}$, $R^{13}$, $R^{14}$, $R^{15}$, $R^{19}$, $R^{20}$, $R^{21}$, $R^{22}$, $R^{23}$ or $R^{24}$ is an aralkyl group wherein the "lower alkyl group" defined above is substituted by the "aryl group" defined above at optional position(s), and, for example, benzyl, 1- or 2-phenethyl, 1-, 2- or 3-phenylpropyl, 1- or 2-naphthylmethyl, benzhydryl, trityl and the like can be mentioned.

The aralkyl group optionally has substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

As the "heteroaryl group" of the "heteroaryl group optionally having substituent(s)" for $R^3$, $R^8$, $R^9$, $R^{10}$, $R^{11}$, $R^{12}$, $R^{13}$, $R^{14}$, $R^{15}$, $R^{19}$, $R^{20}$, $R^{21}$, $R^{22}$, $R^{23}$ or $R^{24}$ for example, a 5- to 10-membered aromatic heterocyclic group containing, besides carbon atoms, 1 to 3 hetero atoms selected from an oxygen atom, a sulfur atom and a nitrogen atom, and a fused heterocyclic group thereof and the like can be mentioned. For example, 2- or 3-thienyl, 2- or 3-furyl, 1-, 2- or 3-pyrrolyl, 1-, 2-, 4- or 5-imidazolyl, 2-, 4- or 5-oxazolyl, 2-, 4- or 5-thiazolyl, 1-, 3-, 4- or 5-pyrazolyl, 3-, 4- or 5-isoxazolyl, 3-, 4- or 5-isothiazolyl, 1,2,4-triazol-1, 3, 4 or 5-yl, 1,2,3-triazol-1, 2 or 4-yl, 1H-tetrazol-1 or 5-yl, 2H-tetrazol-2 or 5-yl, 2-, 3- or 4-pyridyl, 2-, 4- or 5-pyrimidinyl, 1-, 2-, 3-, 4-, 5-, 6- or 7-indolyl, 2-, 3-, 4-, 5-, 6- or 7-benzofuryl, 2-, 3-, 4-, 5-, 6- or 7-benzothienyl, 1-, 2-, 4-, 5-, 6- or 7-benzimidazolyl, 2-, 3-, 4-, 5-, 6-, 7- or 8-quinolyl, 1-, 3-, 4-, 5-, 6-, 7- or 8-isoquinolyl and the like can be mentioned.

The heteroaryl group optionally has substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

The "substituent" of the "heteroaryl group optionally having substituent(s)" for $R^3$ is preferably an alkyl group, a haloalkyl group, a nitro group, a cyano group, —COOR$^{25}$ wherein $R^{25}$ is as defined above, and the like.

As the "hetero atom" of the "hetero atom optionally having substituent(s)" for $R^8$, $R^9$ or $R^{10}$, for example, a nitrogen atom, an oxygen atom, a sulfur atom and the like can be mentioned.

As the substituents that the hetero atom may have, for example, the "lower alkyl group optionally having substituent (s)", "aralkyl group optionally having substituent(s)", "aryl group optionally having substituent(s)" and "heteroaryl group optionally having substituent(s)", each defined above, and the like can be mentioned.

As the "hetero atom" of the "hetero atom having substituent(s)" for $R^{16}$, for example, a nitrogen atom, an oxygen atom, a sulfur atom and the like can be mentioned.

As the substituents that the hetero atom has, for example, the "lower alkyl group optionally having substituent(s)", "aralkyl group optionally having substituent(s)", "aryl group optionally having substituent(s)" and "heteroaryl group optionally having substituent(s)", each defined above, —COOR$^{26}$, —COR$^{27}$, —SO$_2$R$^{28}$ wherein $R^{26}$, $R^{27}$ and $R^{28}$ are the same or different and each is a lower alkyl group as defined above, and the like can be mentioned.

Examples of the "aliphatic heterocycle" of the "aliphatic heterocycle optionally having substituent(s)", which $R^1$ and $R^2$ optionally form together with the nitrogen atom they are bonded to, include a 5- to 10-membered aliphatic heterocycle containing carbon atoms and at least one nitrogen atom and, besides these, optionally containing 1 to 3 hetero atoms selected from an oxygen atom, a sulfur atom and a nitrogen atom, such as pyrrolidine, piperidine, morpholine, thiomorpholine, piperazine and the like.

The aliphatic heterocycle is optionally condensed with an aromatic hydrocarbon, and as such an aromatic hydrocarbon, benzene, naphthalene, biphenyl, binaphthyl and the like can be mentioned.

The aliphatic heterocycle optionally has substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

As the "aliphatic heterocycle optionally having substituent (s)", which $R^{21}$ and $R^{22}$ optionally form together with the nitrogen atom they are bonded to, those similar to the above-mentioned can be mentioned.

As the "homocyclic ring" of the "homocyclic ring optionally having substituent(s)", which $R^4$ and $R^5$ optionally form together with the asymmetric carbons they are respectively bonded to, for example, a cycloalkane having 3 to 7 carbon atoms (e.g., cyclopropane, cyclobutane, cyclopentane, cyclohexane, cycloheptane etc.), a cycloalkene having 4 to 7 carbon atoms (e.g., cyclobutene, cyclopentene, cyclohexene, cycloheptene etc.) and the like, each containing the asymmetric carbons of C* and C** in asymmetric urea compound (I), can be mentioned. Preferred are cyclopropane, cyclobutane, cyclopentane, cyclohexane and the like, and more preferred are cyclohexane and the like.

As the "heterocycle" of the "heterocycle optionally having substituent(s)", which $R^4$ and $R^5$ optionally form together with the asymmetric carbons they are respectively bonded to, for example, a 5- to 10-membered heterocycle containing the asymmetric carbons of C* and C** in asymmetric urea compound (I), and containing, besides carbon atoms, 1 to 3 hetero atoms selected from an oxygen atom, a sulfur atom and a nitrogen atom, (e.g., tetrahydropyran, tetrahydrofuran, pyrrolidine, piperidine and the like) can be mentioned.

The "homocyclic ring" and "heterocycle" are optionally further condensed with an aromatic hydrocarbon (e.g., benzene, aphthalene, biphenyl, binaphthyl etc.).

The "homocyclic ring" and "heterocycle" optionally have substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

As the "homocyclic ring" of the "homocyclic ring optionally having substituent(s)", which $R^{16}$ and $R^{17}$ optionally form together with the carbon atoms they are respectively bonded to, a homocyclic ring substituted by oxo, for example, a cycloalkanone having 3 to 7 carbon atoms (e.g., cyclopropanone, cyclobutanone, cyclopentanone, cyclohexanone, cycloheptanone etc.), a cycloalkenone having 4 to 7 carbon atoms (e.g., cyclobutenone, cyclopentenone, cyclohexenone, cycloheptenone etc.) and the like can be mentioned. Preferred are cyclopropanone, cyclobutanone, cyclopentanone, cyclohexanone and the like, and more preferred are cyclohexanone and the like.

As the "heterocycle" of the "heterocycle optionally having substituent(s)", which $R^{16}$ and $R^{17}$ optionally form together with the carbon atoms they are respectively bonded to, for example, a 5- to 10-membered heterocycle substituted by oxo and containing, besides carbon atoms, 1 to 3 hetero atoms selected from an oxygen atom, a sulfur atom and a nitrogen atom (e.g., tetrahydropyranone, tetrahydrofuranone, pyrrolidone, piperidone) and the like can be mentioned.

The "homocyclic ring" and "heterocycle" are optionally further condensed with an aromatic hydrocarbon (e.g., benzene, naphthalene, biphenyl, binaphthyl etc.).

The "homocyclic ring" and "heterocycle" optionally have substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

In compound (II), as the "homocyclic ring" of the "homocyclic ring optionally having substituent(s)", which $R^9$ and $R^{10}$ optionally form together with the carbon atoms they are respectively bonded to, a homocyclic ring having the double bond in compound (II), for example, a cycloalkene having 3 to 7 carbon atoms (e.g., cyclopropene, cyclobutene, cyclopentene, cyclohexene, cycloheptene etc.) and the like can be mentioned.

In compound (II), as the "heterocycle" of the "heterocycle optionally having substituent(s)", which $R^9$ and $R^{10}$ optionally form together with the carbon atoms they are respectively bonded to, a 5- to 10-membered heterocycle having the double bond in compound (II) and containing, besides carbon atoms, 1 to 3 hetero atoms selected from an oxygen atom, a sulfur atom and a nitrogen atom, (e.g., 5,6-dihydro-2H-pyran, 3,4-dihydro-2H-pyran, 2,3- or 2,5-dihydrofuran, 2- or 3-pyrroline, 1,2,3,4- or 1,2,3,6-tetrahydropyridine and the like) can be mentioned.

The "homocyclic ring" and "heterocycle" are optionally further condensed with an aromatic hydrocarbon (e.g., benzene, naphthalene, biphenyl, binaphthyl etc.).

The "homocyclic ring" and "heterocycle" optionally have substituent(s) at substitutable position(s), and as such substituent(s), the substituents recited for the above-mentioned "aryl group optionally having substituent(s)" can be mentioned. The number of substituents is not particularly limited, but is preferably 1 to 3. When it is 2 or more, the substituents may be the same or different.

In compound (II), the "electron withdrawing group" for $R^8$, $R^9$, $R^{10}$ or EWG is not particularly limited as long as it sufficiently absorbs the electron of the double bond in compound (II), so that the conjugate addition of nucleophilic reagent (III) to the double bond can be afforded, and, for example, a nitro group, a cyano group, $-COR^{11}$, $-SO_2R^{12}$, $-COOR^{13}$ and $-PO(OR^{14})(OR^{15})$ wherein each symbol is as defined above, and the like can be mentioned, which may be the same or different. For $R^8$, $R^9$ or $R^{10}$, a nitro group is preferable; and for EWG, a nitro group and $-COR^{11}$ wherein $R^{11}$ is as defined above are preferable, and a nitro group is more preferable.

In compound (II), when the "electron withdrawing group" for EWG is $-COR^{11}$ wherein each symbol is as defined above, $R^{11}$ and $R^8$, or $R^{11}$ and $R^{10}$, optionally form, together with the carbon atom(s) they are respectively bonded to, a "homocyclic ring having an electron withdrawing group and optionally having substituent(s)".

As the "homocyclic ring having an electron withdrawing group" of the "homocyclic ring having an electron withdrawing group and optionally having substituent(s)", which $R^{11}$ and $R^8$ optionally form together with the carbon atoms they are respectively bonded to, a homocyclic ring having carbonyl as an electron withdrawing group and optionally having the double bond in compound (II), for example, a cycloalkenone having 4 to 7 carbon atoms (e.g., cyclobutenone, 2-cyclopenten-1-one, 2-cyclohexen-1-one, 2-cyclohepten-1-one and the like) can be mentioned.

As the "homocyclic ring having an electron withdrawing group" of the "homocyclic ring having an electron withdrawing group and optionally having substituent(s)", which $R^{11}$ and $R^{10}$ optionally form together with the carbon atom they are respectively bonded to, a homocyclic ring having carbonyl as an electron withdrawing group, for example, a cycloalkanone having 4 to 7 carbon atoms (e.g., cyclobutanone, 2-cyclopentanone, cyclohexanone, cycloheptanone and the like) can be mentioned.

The "homocyclic ring having an electron withdrawing group" is optionally further condensed with an aromatic hydrocarbon (e.g., benzene, naphthalene, biphenyl, binaphthyl etc.).

The "homocyclic ring having an electron withdrawing group" optionally has substituent(s) at substitutable position (s), and as such substituent(s), the substituents recited for the above-mentioned "aryl group optionally having substituent (s)" can be mentioned. The number of substituents is not particularly limited, but is preferably 1 to 3. When it is 2 or more, the substituents may be the same or different.

The "asymmetric carbon" of C*, C or C* each has an independent absolute configuration, and is not particularly limited. The absolute configurations of C* and C** in asymmetric urea compound (I) can be appropriately selected to obtain asymmetric compound (IV) having a desired configuration.

The asymmetric urea compound (I), compound (II) and asymmetric compound (IV) may be in the form of a salt. As such a salt, for example, inorganic acid salts (e.g., hydrochloride, sulfate, nitrate, phosphate etc.); organic acid salts (e.g., acetate, propionate, methanesulfonate, 4-toluenesulfonate, oxalate, maleate etc.); alkali metal salts (e.g., sodium salt, potassium salt etc.); alkaline earth metal salts (e.g., calcium salt, magnesium salt etc.); organic base salts (e.g., trimethylamine salt, triethylamine salt, pyridine salt, picoline salt, dicyclohexylamine salt etc.) and the like can be mentioned.

X in asymmetric urea compound (I) is preferably a sulfur atom.

$R^4$ and $R^5$ in asymmetric urea compound (I) preferably form, together with the asymmetric carbons they are respectively bonded to, a homocyclic ring optionally having substituent(s) or a heterocycle optionally having substituent(s); they more preferably form, together with the asymmetric carbons they are respectively bonded to, a homocyclic ring optionally having substituent(s); they more preferably form, together with the asymmetric carbons they are respectively bonded to, cyclopropane, cyclobutane, cyclopentane or cyclohexane; and they still more preferably form cyclohexane together with the asymmetric carbons they are respectively bonded to.

When $R^4$ and $R^5$ form cyclohexane together with the asymmetric carbons they are respectively bonded to, $R^6$ and $R^7$ are each preferably a hydrogen atom, and more preferably, the absolute configurations of C* and C** are both S-configurations or both R-configurations.

$R^1$ and $R^2$ in asymmetric urea compound (I) are preferably a lower alkyl group optionally having substituent(s), or form, together with the nitrogen atom they are bonded to, an aliphatic heterocycle optionally having substituent(s) and optionally condensed with an aromatic hydrocarbon, more preferably methyl, ethyl or isopropyl, or form isoindoline together with the nitrogen atom they are bonded to, still more preferably methyl or isopropyl.

$R^3$ in asymmetric urea compound (I) is preferably an aryl group optionally having substituent(s), more preferably a phenyl group optionally having substituent(s), more preferably a phenyl group substituted by haloalkyl group(s), nitro group(s), cyano group(s) or $-COOR^{25}$ wherein $R^{25}$ is as defined above, more preferably a phenyl group substituted by haloalkyl group(s), still more preferably a phenyl group substituted by trifluoromethyl.

The electron withdrawing group for EWG in compound (II) is preferably a nitro group, a cyano group, $-COR^{11}$, $-SO_2R^{12}$, $-COOR^{13}$ or $-PO(OR^{14})(OR^{15})$ wherein each symbol is as defined above, more preferably a nitro group.

Since C in compound (IV) is an asymmetric carbon, $R^8$ and $R^9$ in compound (II) cannot be the same group simultaneously.

$R^8$, $R^9$ and $R^{10}$ in compound (II) are each preferably an aryl group optionally having substituent(s) or a heteroaryl group optionally having substituent(s), more preferably $R^8$ and $R^{10}$ are each a hydrogen atom, and $R^9$ is an aryl group optionally having substituent(s) or a heteroaryl group optionally having substituent(s).

The nucleophilic reagent (III) is preferably $HCR^{16}$ $(COR^{17})(COR^{18})$, $HOR^{19}$, $HSR^{20}$, $HNR^{21}R^{22}$ or $HC(NO_2)$ $R^{23}R^{24}$ wherein each symbol is as defined above, more preferably $HCR^{16}(COR^{17})(COR^{18})$ wherein each symbol is as defined above.

In a preferable embodiment when nucleophilic reagent (III) is $HCR^{16}(COR^{17})(COR^{18})$ wherein each symbol is as defined above, $R^{16}$ is a hydrogen atom, a lower alkyl group optionally having substituent(s), a halogen atom or a hetero atom having substituent(s), more preferably a hydrogen atom, methyl, chlorine atom, methoxy or tert-butoxycarbonylamino, and $R^{17}$ and $R^{18}$ are each a lower alkyl group or a lower alkoxy group, more preferably a lower alkoxy group, still more preferably methoxy or ethoxy. In another preferable embodiment, $R^{16}$ and $R^{17}$ form, together with the carbon atoms they are respectively bonded to, a homocyclic ring optionally having substituent(s) (the homocyclic ring is optionally condensed with an aromatic hydrocarbon), more preferably 1,2,3,4-tetrahydronaphthalen-1-one.

The asymmetric urea compound (I) of the present invention can be produced according to Production Method 1 shown by the following reaction scheme.

Production Method 1

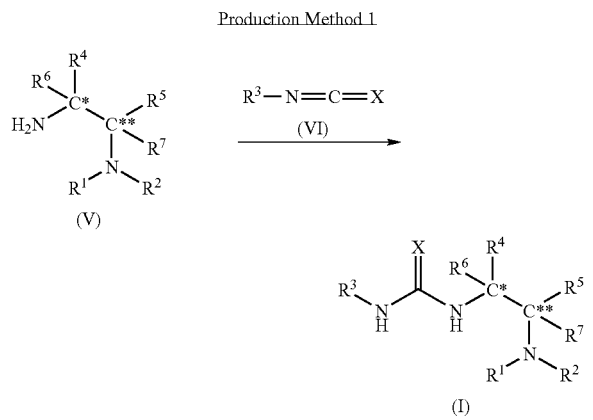

(I)

wherein each symbol is as defined above.

That is, asymmetric urea compound (I) can be synthesized, for example, by reacting a compound represented by the formula (V) [hereinafter to be also referred to as compound (V)] with an isocyanate compound or isothiocyanate compound represented by the formula (VI) [hereinafter to be also referred to as isocyanates (VI)] in a solvent.

In Production Method 1, the order of addition of compound (V) and isocyanates (VI) is not particularly limited, and they may be added to a solvent simultaneously or successively.

The amount of isocyanates (VI) to be used in Production Method 1 is preferably 0.5 mol to 5 mol, more preferably 0.9 mol to 1.5 mol, per 1 mol of compound (V).

As the solvent to be used in Production Method 1, any can be used as long as it does not inhibit the reaction and, for example, halogen solvents such as methylene chloride, chloroform, chlorobenzene, α,α,α-trifluorotoluene and the like; methyl-tert-butyl ether, 1,2-dimethoxyethane, tetrahydrofuran, 1,4-dioxane, ethyl acetate, isopropyl acetate, tert-butyl acetate, toluene, xylene, acetonitrile and the like can be used alone or in a mixture. When a mixed solvent is used, they can be admixed at any ratio.

The amount of the solvent to be used is generally 1 L to 100 L, more preferably 10 L to 30 L, per 1 kg of compound (V).

The reaction temperature in Production Method 1 is generally −78° C. to 100° C., preferably 0° C. to 40° C.

While the reaction time varies depending on the reagent to be used and reaction temperature, it is generally 1 hr to 10 hr.

The asymmetric urea compound (I) produced according to Production Method 1 can be isolated and purified according to a conventional method. For example, asymmetric urea compound (I) can be isolated by pouring a reaction mixture into water to partition the mixture, and washing and concentrating the organic layer under reduced pressure; or by concentrating the reaction mixture. After isolation, the obtained product is purified, for example, by, but not limited to, silica gel column chromatography.

The compound (V), which is a starting material in Production Method 1, can be produced according a known method (e.g., a method described in Tetrahedron, 57, 1765-1769 (2001)). For example, a compound represented by the formula (Va), which is a preferable mode of the present invention:

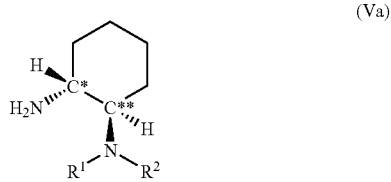

wherein each symbol is as defined above, can be produced according a method described in Tetrahedron Letters, 41, 8431-8434(2000).

The isocyanates (VI), which is the other starting material in Production Method 1, can be synthesized from an amine represented by $R^3$—$NH_2$ wherein $R^3$ is as defined above according to a known method (e.g., a method described in Eur. J. Org. Chem., 3004-3014 (2002)), or a commercially available product can also be used.

Now, the production method of asymmetric compound (IV) of the present invention by an asymmetric conjugate addition reaction (hereinafter to be also simply referred to as the production method of the present invention) is explained.

The production method of the present invention is shown by the following reaction scheme:

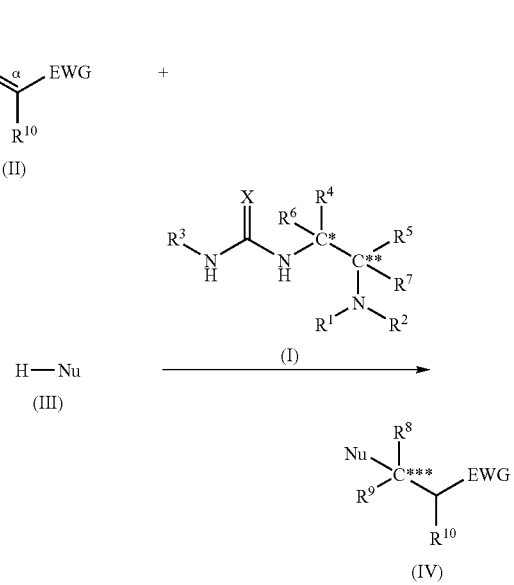

wherein each symbol is as defined above.

That is, according to the production method of the present invention, for example, asymmetric compound (IV) is produced by conjugately adding nucleophilic reagent (III) to compound (II) in the presence of asymmetric urea compound (I) in a solvent or without a solvent.

The asymmetric compound (IV) produced according to the production method of the present invention is optically active, wherein the optical purity is not particularly limited. As an enantiomer excess measured by HPLC chiral analysis, it is generally not less than 50% e.e., preferably not less than 90% e.e.

In the production method of the present invention, the conjugate addition means, in compound (II), an addition reaction of nucleophilic reagent (III) to a carbon not bonded to EWG (i.e., β-carbon) from the carbons of the double bond conjugate-bonded to the electron withdrawing group for EWG.

In production method of the present invention, the order of addition of the reagents is not particularly limited, and asymmetric urea compound (I), compound (II) and nucleophilic reagent (III) can be added simultaneously or successively.

The amount of asymmetric urea compound (I) to be used in the production method of the present invention can be a catalytic amount and it is, for example, preferably 0.01 mol to 1.00 mol, more preferably 0.05 mol to 0.20 mol, per 1 mol of compound (II). When the amount of asymmetric urea compound (I) to be used is less than this range, the reaction tends to be slow and when it exceeds this range, the effect tends to be less than comparable to its amount of use, which is economically disadvantageous.

The amount of nucleophilic reagent (III) to be used in the production method of the present invention is preferably 1 mol to 10 mol, more preferably 1.2 mol to 3 mol, per 1 mol of compound (II). When the amount of nucleophilic reagent (III) to be used is less than the range, the reaction tends to be incomplete, and when it exceeds this range, the effect tends to be less than comparable to its amount of use, which is economically disadvantageous.

The production method of the present invention can be performed in a solvent or without a solvent. The production method performed without a solvent is economically advantageous because the solvent is not necessary, and is industrially advantageous because the volume efficiency can be increased.

When a solvent is used for the production method of the present invention, the solvent may be any as long as it does not inhibit the reaction and, for example, halogen solvents such as methylene chloride, chloroform, chlorobenzene, α,α,α-trifluorotoluene and the like; methyl-tert-butyl ether, 1,2-dimethoxyethane, tetrahydrofuran, 1,4-dioxane, ethyl acetate, isopropyl acetate, tert-butyl acetate, toluene, xylene, acetonitrile and the like can be used alone or in a mixture. In view of superior yield and stereoselectivity, toluene or methylene chloride is preferably used.

When a mixed solvent is used, they may be mixed at any ratio.

The amount of the solvent to be used is generally 1 L to 100 L, more preferably 10 L to 30 L, per 1 kg of compound (II).

The reaction temperature in the production method of the present invention is generally −78° C. to 100° C., preferably 0° C. to 40° C.

While the reaction time varies depending on the reagent to be used and reaction temperature, it is generally 0.1 hr to 100 hr.

The asymmetric compound (IV) produced according the production method of the present invention can be isolated and purified according to a conventional method. For example, asymmetric compound (IV) can be isolated by pouring a reaction mixture into water to partition the mixture, and washing and concentrating the organic layer under reduced pressure; or by concentrating the reaction mixture. After isolation, the obtained product is purified, for example, by, but not limited to, silica gel column chromatography.

The asymmetric urea compound (I) can be easily separated and recovered during isolation and purification of asymmetric compound (IV). For example, since basic amine is present in asymmetric urea compound (I), compound (I) can be separated from asymmetric compound (IV) during extraction by transferring compound (I) in the form of a salt into the aqueous layer by treating the mixture with an aqueous acidic solution (e.g., hydrochloric acid, nitric acid, sulfuric acid etc.). After neutralization of the aqueous solution, it is extracted with an organic solvent (e.g., ethyl acetate, toluene, chloroform, methylene chloride etc.) to recover asymmetric urea compound (I). It may also be separated and recovered by silica gel column chromatography.

The asymmetric urea compound (I) separated and recovered in this manner can be re-used for the production method of the present invention. That is, since asymmetric urea compound (I) of the present invention is non-metal, degradation of catalytic activity as observed in metal catalysts etc. does not occur easily, and compound (I) can be re-used as many times as desired upon recovery, which is economically advantageous.

As asymmetric urea compound (I), which is a starting material in the production method of the present invention, for example, one produced according to the above-mentioned Production Method 1 can be used.

The compound (II), which is a starting material in the production method of the present invention, can be produced according a known method, such as dehydrative condensation of a carbonyl compound represented by the following formula (VII) and an active methylene compound represented by the following formula (VIII):

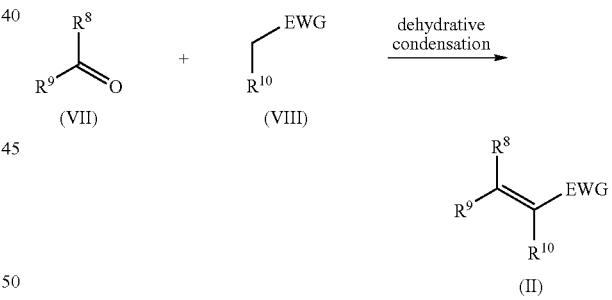

wherein each symbol is as defined above.

As such a dehydrative condensation reaction, aldol condensation, Knoevenagel reaction, Perkin reaction and the like, and modification of these methods can be mentioned.

In addition, commercially available products may be used for trans-β-nitrostyrene and the like, which are preferable examples of compound (II).

The nucleophilic reagent (III), which is a starting material in the present invention, can be produced according a known method, such as the methods described in Tetrahedron Letters, 39, 8013-8016 (1998), Bull. Chem. Soc. Jpn., 61, 4029-4035 (1988) and the like. In addition, commercially available products may be used for diethyl malonate and the like, which are preferable examples of nucleophilic reagent (III).

The asymmetric compound (IV) produced according to the production method of the present invention is useful as an intermediate for synthesizing amines, amino acids, pharmaceutical agents, agricultural chemicals, food additives and the like. For example, ethyl (R)-3-(3-cyclopentyl-4-methoxyphenyl)-2-ethoxycarbonyl-4-nitrobutyrate, which is one example of compound (IV), can be converted to (R)-Rolipram (antidepressant) according to a method described in Journal of the American Chemical Society, vol. 124, No. 44, p. 13097-13105 (2002).

EXAMPLES

The present invention is explained more specifically in the following by referring to Examples, which are not to be construed as limitative.

Example 1A (R,R)-trans-1-[3,5-bis(trifluoromethyl)phenyl]-3-[2-(N,N-dimethylamino)cyclohexyl]thiourea

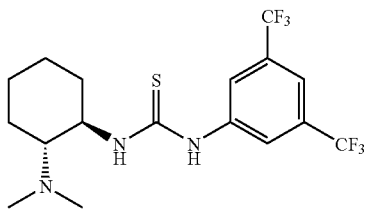

To a solution (1.0 ml) of 3,5-bis(trifluoromethyl)phenyl-isothiocyanate (605 mg, 2.23 mmol) in dry tetrahydrofuran was added (R,R)-trans-N,N-dimethyl-1,2-diaminocyclohexane (317 mg, 2.23 mmol) under an argon atmosphere. The reaction mixture was stirred at room temperature for 3 hr, and concentrated under reduced pressure. The obtained residue was purified by silica gel column chromatography (elution solvent: chloroform/methanol/triethylamine=100/5/1) to give the title compound as a white amorphous solid (597 mg, yield 65%). $[\alpha]_D^{16}$ −32.7 (c 0.99, CHCl$_3$);

$^1$H-NMR (500 MHz, DMSO-d$_6$) δ 10.0 (s, 1H), 8.21 (s, 1H), 8.17 (s, 2H), 7.66 (s, 1H), 4.09 (brs, 1H), 2.54 (brs, 1H), 2.21 (s, 7H), 1.82 (brs, 1H), 1.74 (brs, 1H), 1.63 (brd, J=11.0 Hz, 1H), 1.31-1.01 (m, 4H) ppm;

$^{13}$C-NMR (126 MHz, DMSO-d$_6$) δ 178.6, 142.0, 130.8, 130.5, 130.3, 130.0, 126.5, 124.3, 122.2, 120.9, 120.0, 115.3, 65.0, 55.3, 45.7, 31.6, 24.6, 24.5, 21.0 ppm;

IR (CHCl$_3$) ν 3402, 3200, 2942, 2865, 1528, 1469, 1383, 1278 cm$^{-1}$;

MS (FAB$^+$) 414 (MH$^+$, 100);

Elemental analysis

Calculated (for C$_{17}$H$_{21}$F$_6$N$_3$S): C, 49.39; H, 5.12; N, 10.16; F, 27.57.

Found: C, 49.36; H, 5.28; N, 10.11; F, 27.71.

Example 1B (R,R)-trans-1-[3,5-bis(trifluoromethyl)phenyl]-3-[2-(N,N-dimethylamino)cyclohexyl]urea

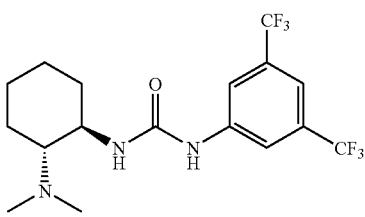

To a solution (0.60 ml) of 3,5-bis(trifluoromethyl)phenyl-isocyanate (0.26 ml, 1.5 mmol) in dry benzene was added (R,R)-trans-N,N-dimethyl-1,2-diaminocyclohexane (213 mg, 1.5 mmol) under an argon atmosphere. The reaction mixture was stirred at room temperature for 1 hr, and concentrated under reduced pressure. The obtained residue was purified by silica gel column chromatography (CHCl$_3$/MeOH=20/1-7/1) to give the title compound as a white amorphous solid.

$[\alpha]_D^{25}$ −35.3 (c 0.93, CHCl$_3$);

$^1$H-NMR (500 MHz, DMSO-d$_6$) δ 9.39 (s, 1H), 8.02 (s, 2H), 7.51 (s, 1H), 6.21 (d, J=5.5 Hz, 1H), 3.35 (ddd, J=15.2, 10.5, 4.3 Hz, 1H), 2.28 (dt, J=3.1, 10.2 Hz, 1H), 2.18 (brs, 1H), 2.15 (s, 6H), 1.85-1.66 (m, 2H), 1.63-1.52 (m, 1H), 1.31-0.96 (m, 4H) ppm;

$^{13}$C-NMR (126 MHz, DMSO-d$_6$) δ 154.9, 142.9, 131.3, 131.1, 130.8, 130.5, 126.9, 124.7, 122.5, 120.4, 117.12, 117.09, 113.4, 113.3, 65.6, 50.9, 39.9, 33.2, 24.9, 24.5, 21.4 ppm;

IR (CHCl$_3$) ν 3424, 3332, 2939, 2864, 2792, 1695, 1549, 1473 cm$^{-1}$;

MS (FAB$^+$) 398 (MH$^+$, 100);

Elemental analysis

Calculated (for C$_{17}$H$_{21}$F$_6$N$_3$O): C, 51.38; H, 5.33; N, 10.57; F, 28.69.

Found: C, 51.30; H, 5.22; N, 10.58; F, 28.46.

Example 2

(R,R)-trans-1-[3,5-bis(trifluoromethyl)phenyl]-3-[2-(isoindolin-2-yl)cyclohexyl]thiourea

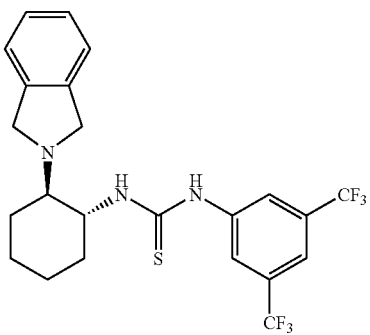

In the same manner as in Example 1A except that (R,R)-trans-N-[2-(isoindolin-2-yl)cyclohexyl]amine was used instead of (R,R)-trans-N,N-dimethyl-1,2-diaminocyclohexane, the title compound was obtained as colorless crystals (yield 21%). melting point: 154-156° C. (n-hexane/ethyl acetate).

$[\alpha]_D^{17}$ −18.1 (c 1.01, CHCl$_3$)

$^1$H-NMR (500 MHz, DMSO-d$_6$) δ 10.00 (s, 1H), 8.30 (d, J=7.0 Hz, 1H), 8.15 (s, 2H), 7.67 (s, 1H), 7.24 (dd, J=3.4, 5.2 Hz, 2H), 7.18 (dd, J=3.2, 5.3 Hz, 2H), 4.31 (brs, 1H), 4.04 (d, J=11.6 Hz, 2H), 3.99 (d, J=11.9 Hz, 2H), 2.87 (dt, J=2.7, 9.8 Hz, 1H), 2.18 (brd, J=8.2 Hz, 1H), 1.88 (brd, J=11.6 Hz, 1H), 1.76 (brd, J=7.9 Hz, 1H), 1.65 (m, 1H), 1.44 (m, 1H), 1.30 (m, 3H) ppm;

$^{13}$C-NMR (126 MHz, DMSO-d$_6$) δ 184.1, 147.0, 144.9, 135.6, 135.3, 131.6, 129.5, 127.5, 127.3, 126.4, 120.8, 65.6, 60.5, 58.3, 29.0, 28.82, 28.77, 28.1 ppm;

IR (CHCl$_3$) ν 3402, 2941, 2862, 1539, 1495, 1470, 1382, 1279, 1179, 1140 cm$^{-1}$;

MS (FAB$^+$) 488 (MH$^+$, 100);

Elemental analysis

Calculated (for C$_{23}$H$_{23}$F$_6$N$_3$S): C, 56.67; H, 4.76; N, 8.62; F, 23.38.

Found: C, 56.66; H, 4.74; N, 8.46; F, 23.45.

Example 3

(R,R)-trans-1-[3,5-bis(trifluoromethyl)phenyl]-3-[2-(N-isopropyl-N-methylamino)cyclohexyl]thiourea

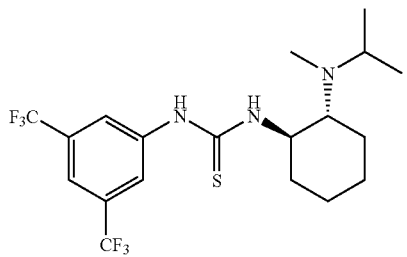

In the same manner as in Example 1A except that (R,R)-trans-N-isopropyl-N-methyl-1,2-diaminocyclohexane was used instead of (R,R)-trans-N,N-dimethyl-1,2-diaminocyclohexane, the title compound was obtained as a colorless amorphous solid (yield 64%).

$[\alpha]_D^{26}$ +51.3 (c 0.98, CHCl$_3$);

$^1$H-NMR (500 MHz, DMSO-d$_6$) δ 10.10 (s, 1H), 8.21 (s, 2H), 7.87 (s, 1H), 7.69 (s, 1H), 4.08 (brs, 1H), 2.96-2.78 (m, 1H), 2.62 (brs, 1H), 2.37-2.07 (m, 4H), 1.82 (brd, J=10.7 Hz, 1H), 1.71 (brd, J=6.7 Hz, 1H), 1.61 (brd, J=7.7 Hz, 1H), 1.31-1.07 (m, 4H), 0.98 (d, J=6.1 Hz, 6H) ppm;

$^{13}$C-NMR (126 MHz, DMSO-d$_6$) δ 179.2, 142.0, 130.7, 130.5, 130.2, 129.9, 126.6, 124.4, 122.2, 121.4, 120.1, 115.6, 63.6, 55.0, 31.8, 31.3, 25.6, 25.0, 24.5, 21.4, 20.1 ppm;

IR (CHCl$_3$) ν 3402, 2943, 2863, 1496, 1470, 1384, 1279, 1179, 1141 cm$^{-1}$;

MS (FAB$^+$) 442 (MH$^+$, 100);

HRMS (FAB$^+$)

Calculated (for [C$_{19}$H$_{26}$F$_6$N$_3$S]$^+$): 442.1752.

Found: 442.1743.

Example 4

(R,R)-trans-1-[2-(N,N-dimethylamino)cyclohexyl]-3-phenylthiourea

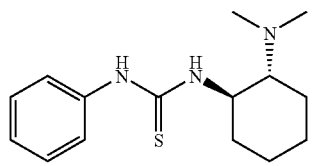

In the same manner as in Example 1A except that phenylisothiocyanate was used instead of 3,5-bis(trifluoromethyl)phenylisothiocyanate, the title compound was obtained as a colorless amorphous solid (yield 95%).

$[\alpha]_D^{21}$ −112 (c 0.98, CHCl$_3$);

$^1$H-NMR (500 MHz, DMSO-d$_6$) δ 7.38 (t, J=7.8 Hz, 2H), 7.30-7.14 (m, 4H), 6.79 (s, 1H), 3.86 (brs, 1H), 2.73 (brs, 1H), 2.33 (dt, J=2.9, 11.1 Hz, 1H), 2.24 (s, 6H), 1.93-1.75 (m, 2H), 1.70 (brd, J=13.7 Hz, 1 Hz), 1.42-1.28 (m, 1H), 1.28-1.11 (m, 2H), 1.10-0.96 (m, 1H) ppm;

$^{13}$C-NMR (126 MHz, DMSO-d$_6$) δ 179.1, 137.4, 128.9, 125.5, 124.3, 66.0, 55.4, 39.4, 32.4, 24.6, 24.2, 21.0 ppm;

IR (CHCl$_3$) ν 3411, 2939, 2864, 2790, 1529, 1500 cm$^{-1}$;

MS (FAB$^+$) 278 (MH$^+$, 100);

HRMS (FAB$^+$)

Calculated (for [C$_{15}$H$_{24}$N$_3$S]$^+$): 278.1691.

Found: 278.1692.

Example 5

1-[(R,R)-2-(N,N-dimethylamino)cyclohexyl]-3-(2-methoxyphenyl)thiourea

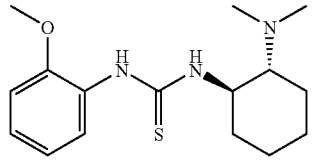

In the same manner as in Example 1A except that 2-methoxyphenylisothiocyanate was used instead of 3,5-bis(trifluoromethyl)phenylisothiocyanate, the title compound was obtained as a colorless amorphous solid (yield 100%).

$[\alpha]_D^{19}$ −116 (c 1.10, CHCl$_3$)

$^1$H-NMR (500 MHz, DMSO-d$_6$) δ 8.19 (s, 1H), 7.41 (d, J=7.3 Hz, 1H), 7.15-6.92 (m, 2H), 6.89-6.69 (m, 2H), 3.79 (brs, 1H), 3.67 (s, 3H), 2.60 (d, J=10.7 Hz, 1H), 2.35-2.22 (m, 1H), 2.09 (s, 6H), 1.83-1.60 (m, 2H), 1.54 (d, J=13.7 Hz, 1H), 1.20 (q, J=13.0 Hz, 1H), 1.15-0.97 (m, 2H), 0.96-0.81 (m, 1H) ppm;

$^{13}$C-NMR (126 MHz, DMSO-d$_6$) δ 179.5, 151.5, 126.3, 125.0, 124.1, 120.2, 111.1, 66.3, 55.9, 55.3, 39.5, 32.3, 24.8, 24.3, 21.2 ppm;

IR (CHCl$_3$) ν 3406, 2939, 2863, 1600, 1512 cm$^{-1}$;

MS (FAB$^+$) 308 (MH$^+$, 100);

HRMS (FAB$^+$)

Calculated (for [C$_{16}$H$_{26}$N$_3$OS]$^+$): 308.1757.
Found: 308.1790.

Comparative Example 1

(R,R)-trans-N-[2-(N',N'-dimethylamino)cyclohexyl]
acetamide

In the same manner as in Example 1A except that acetic anhydride was used instead of 3,5-bis(trifluoromethyl)phenylisothiocyanate, the title compound was obtained as a colorless amorphous solid (yield 87%).

Comparative Example 2

1-[3,5-bis(trifluoromethyl)phenyl]-3-cyclohexylthiourea

In the same manner as in Example 1A except that cyclohexylamine was used instead of (R,R)-trans-N,N-dimethyl-1,2-diaminocyclohexane, the title compound was obtained as colorless crystals (yield 88%).

Example 6A ethyl (S)-2-ethoxycarbonyl-4-nitro-3-phenylbutyrate

To a solution (0.40 ml) of trans-β-nitrostyrene (29.8 mg, 0.20 mmol) and diethyl malonate (0.061 ml, 0.40 mmol) in toluene was added, as an asymmetric catalyst, (R,R)-trans-1-[3,5-bis(trifluoromethyl)phenyl]-3-[2-(N,N-dimethylamino)cyclohexyl]thiourea (8.2 mg, 0.02 mmol) obtained in Example 1A at room temperature under an argon atmosphere. After 24 hr, the reaction mixture was concentrated under reduced pressure. The residue was purified by preparative TLC (elution solvent: n-hexane/diethyl ether) to give the title compound as colorless needle crystals (53.3 mg, yield 86%). The yield and optical purity are shown in Tables 1-3. melting point: 45-47° C. (n-hexane/diethyl ether)
HPLC analysis conditions:
column: CHIRALCEL AD (manufactured by DAICEL CHEMICAL INDUSTRIES, LTD.),
mobile phase: n-hexane/ethanol=90/10,
flow rate: 1.0 ml/min,
detection: λ=254 nm,
retention time: (S)-isomer (main peak); 11.1 min, (R)-isomer; 13.9 min.
[α]$_D^{30}$ −6.00 (c 1.00, CHCl$_3$)
$^1$H-NMR (500 MHz, DMSO-d$_6$) δ 7.42-7.10 (m, 5H), 4.93 (dd, J=4.6, 13.1 Hz, 1H), 4.86 (dd, J=9.2, 13.1 Hz, 1H), 4.33-4.15 (m, 3H), 4.00 (q, J=7.2 Hz, 2H), 3.82 (d, J=9.5 Hz, 1H), 1.25 (t, J=7.2 Hz, 3H), 1.03 (t, J=7.2 Hz, 3H) ppm;
$^{13}$C-NMR (126 MHz, DMSO-d$_6$) δ 167.4, 166.7, 136.2, 128.8, 128.2, 127.9, 77.6, 62.0, 61.8, 54.9, 42.9, 13.9, 13.6 ppm;
IR (CHCl$_3$) ν 2989, 2938, 1731, 1557 cm$^{-1}$;
MS (FAB$^+$) 310 (MH$^+$, 100);
Elemental analysis
Calculated (for C$_{15}$H$_{19}$NO$_6$): C, 58.24; H, 6.19; N, 4.53.
Found: C, 58.43; H, 6.20; N, 4.56.

Example 6B ethyl (S)-2-ethoxycarbonyl-4-nitro-3-phenylbutyrate

To a solution (0.40 ml) of trans-β-nitrostyrene (29.8 mg, 0.20 mmol) and diethyl malonate (0.061 ml, 0.40 mmol) in toluene was added, as an asymmetric catalyst, (R,R)-trans-1-[3,5-bis(trifluoromethyl)phenyl]-3-[2-(N,N-dimethylamino)cyclohexyl]urea (7.9 mg, 0.02 mmol) obtained in Example 1B at room temperature under an argon atmosphere. After 24 hr, the reaction mixture was concentrated under reduced pressure. The residue was purified by preparative TLC (elution solvent: n-hexane/ethyl acetate=5/1) to give the title compound as colorless needle crystals (53.8 mg, 87%, 91% ee). The yield and optical purity are shown in Table 1.

Example 7 ethyl (S)-2-ethoxycarbonyl-4-nitro-3-phenylbutyrate

In the same manner as in Example 6A except that 0.20 mmol of diethyl malonate was used, the title compound was obtained. The yield and optical purity are shown in Table 1.

Example 8 ethyl (S)-2-ethoxycarbonyl-4-nitro-3-phenylbutyrate

In the same manner as in Example 7 except that methylene chloride was used as a solvent instead of toluene, the title compound was obtained. The yield and optical purity are shown in Table 1.

Example 9 ethyl (S)-2-ethoxycarbonyl-4-nitro-3-phenylbutyrate

In the same manner as in Example 7 except that acetonitrile was used as a solvent instead of toluene, the title compound was obtained. The yield and optical purity are shown in Table 1.

Example 10 ethyl (S)-2-ethoxycarbonyl-4-nitro-3-phenylbutyrate

In the same manner as in Example 7 except that tetrahydrofuran was used as a solvent instead of toluene, the title compound was obtained. The yield and optical purity are shown in Table 1.

TABLE 1

| Example | solvent | nucleophilic reagent equivalent | yield (%) | optical purity (% ee) |
|---------|---------|---------------------------------|-----------|----------------------|
| 6A | toluene | 2 | 86 | 93 |
| 6B | toluene | 2 | 87 | 91 |
| 7 | toluene | 1 | 60 | 92 |
| 8 | methylene chloride | 1 | 53 | 90 |
| 9 | acetonitrile | 1 | 47 | 75 |
| 10 | tetrahydrofuran | 1 | 29 | 88 |

It is clear that the use of 2 equivalents of the nucleophilic reagent increased the yield. When toluene or methylene chloride was used, the yield and selectivity were superior to the use of acetonitrile or tetrahydrofuran.

Example 11 ethyl (S)-2-ethoxycarbonyl-4-nitro-3-phenylbutyrate

In the same manner as in Example 6A except that the reaction time was set to 48 hr and (R,R)-trans-1-[3,5-bis (trifluoromethyl)phenyl]-3-[2-(isoindolin-2-yl)cyclohexyl] thiourea obtained in Example 2 was used as an asymmetric catalyst, the title compound was obtained. The yield and optical purity are shown in Table 2.

Example 12 ethyl (S)-2-ethoxycarbonyl-4-nitro-3-phenylbutyrate

In the same manner as in Example 6A except that the reaction time was set to 48 hr and (R,R)-trans-1-[3,5-bis (trifluoromethyl)phenyl]-3-[2-(N-isopropyl-N-methylamino)cyclohexyl]thiourea obtained in Example 3 was used as an asymmetric catalyst, the title compound was obtained. The yield and optical purity are shown in Table 2.

Example 13 ethyl (S)-2-ethoxycarbonyl-4-nitro-3-phenylbutyrate

In the same manner as in Example 6A except that the reaction time was set to 48 hr and (R,R)-trans-1-[2-(N,N-dimethylamino)cyclohexyl]-3-phenylthiourea obtained in Example 4 was used as an asymmetric catalyst, the title compound was obtained. The yield and optical purity are shown in Table 2.

Example 14 ethyl (S)-2-ethoxycarbonyl-4-nitro-3-phenylbutyrate

In the same manner as in Example 6A except that the reaction time was set to 48 hr and 1-[(R,R)-2-(N,N-dimethylamino)cyclohexyl]-3-(2-methoxyphenyl)thiourea obtained in Example 5 was used as an asymmetric catalyst, the title compound was obtained. The yield and optical purity are shown in Table 2.

Comparative Example 3 ethyl (S)-2-ethoxycarbonyl-4-nitro-3-phenylbutyrate

In the same manner as in Example 6A except that triethylamine was used instead of the asymmetric catalyst, the title compound was obtained. The yield is shown in Table 2.

Comparative Example 4 ethyl (S)-2-ethoxycarbonyl-4-nitro-3-phenylbutyrate

In the same manner as in Example 6A except that (R,R)-trans-N-[2-(N',N'-dimethylamino)hexyl]acetamide obtained in Comparative Example 1 was used as an asymmetric catalyst, the title compound was obtained. The yield and optical purity are shown in Table 2.

Comparative Example 5 ethyl (S)-2-ethoxycarbonyl-4-nitro-3-phenylbutyrate

In the same manner as in Example 6A except that 1-[3,5-bis(trifluoromethyl)phenyl]-3-cyclohexylthiourea obtained in Comparative Example 2 and 0.1 equivalent of triethylamine were used instead of the asymmetric catalyst, the title compound was obtained. The yield is shown in Table 2.

TABLE 2

| Example | asymmetric catalyst | reaction time (hr) | yield (%) | optical purity (% ee) |
|---|---|---|---|---|
| 6A | Example 1A | 24 | 86 | 93 |
| 11 | Example 2 | 48 | 29 | 91 |
| 12 | Example 3 | 48 | 76 | 87 |
| 13 | Example 4 | 48 | 58 | 80 |
| 14 | Example 5 | 48 | 40 | 52 |
| Comparative Example 3 | TEA | 24 | 17 | — |
| Comparative Example 4 | Comparative Example 1 | 24 | 14 | 35 |
| Comparative Example 5 | Comparative Example 2 + TEA | 24 | 57 | — |

Introduction of bulky substituents into $R^1$ and $R^2$ of asymmetric urea compound (I) tends to result in a decreased yield. When $R^3$ is a substituted phenyl, the use of a compound wherein the phenyl is substituted by methoxy, which is electron-donative, tended to result in decreased yield and stereoselectivity.

A catalyst having an amine moiety or thiourea moiety alone caused a striking decrease in the yield, and when a catalyst having an amine moiety alone and a catalyst having thiourea moiety alone were added simultaneously, the yield was improved but only to a level not comparable to Example 6A and Example 6B.

Example 15 ethyl (S)-3-(2,6-dimethoxyphenyl)-2-ethoxycarbonyl-4-nitrobutyrate

In the same manner as in Example 6A except that the reaction time was set to 72 hr and trans-2,6-dimethoxy-β-nitrostyrene was used instead of trans-β-nitrostyrene, the title compound was obtained as a colorless oil. The yield and optical purity are shown in Table 3.

HPLC analysis conditions:

column: CHIRALCEL AD (manufactured by DAICEL CHEMICAL INDUSTRIES, LTD.), mobile phase: n-hexane/2-propanol=95/5, flow rate: 1.0 ml/min, detection: λ=254 nm, retention time: (S)-isomer (main peak); 12.8 min, (R)-isomer; 15.7 min.

$[\alpha]_D^{24}$ −11.4 (c 1.03, CHCl$_3$)

$^1$H-NMR (500 MHz, DMSO-d$_6$) δ 7.18 (t, J=8.4 Hz, 1H), 6.52 (d, J=8.2 Hz, 2H), 5.08-4.99 (m, 1H), 4.93 (dd, J=12.1, 9.0 Hz, 1H), 4.85 (dd, J=12.1, 4.7 Hz, 1H), 4.32-4.15 (m, 3H), 3.92-3.80 (m, 2H), 3.82 (s, 6H), 1.29 (t, J=7.2 Hz, 3H), 0.95 (t, J=7.0 Hz, 3H) ppm;

$^{13}$C-NMR (126 MHz, DMSO-d$_6$) δ 168.4, 167.3, 158.9, 129.6, 112.5, 104.3, 76.6, 61.8, 61.2, 52.8, 52.5, 33.2, 13.9, 13.5 ppm;

IR (CHCl$_3$) ν 3030, 2985, 2842, 1730, 1555 cm$^{-1}$;

MS (EI$^+$) 369 (M$^+$), 249 (MH$^+$, 100);

Elemental analysis

Calculated (for C$_{17}$H$_{23}$NO$_8$): C, 55.28; H, 6.28; N, 3.79.

Found: C, 55.31; H, 6.13; N, 3.55.

Example 16 ethyl (S)-2-ethoxycarbonyl-3-(1-fluorophenyl)-4-nitrobutyrate

In the same manner as in Example 6A except that the reaction time was set to 12 hr and trans-4-fluoro-β-nitrostyrene was used instead of trans-β-nitrostyrene, the title compound was obtained as a colorless oil. The yield and optical purity are shown in Table 3.

HPLC analysis conditions:
column: CHIRALCEL AD (manufactured by DAICEL CHEMICAL INDUSTRIES, LTD.),
mobile phase: n-hexane/ethanol=90/10,
flow rate: 1.0 ml/min,
detection: λ=254 nm,
retention time: (S)-isomer (main peak); 16.3 min, (R)-isomer; 23.9 min.
$[\alpha]_D^{28}$ −7.20 (c 1.00, CHCl$_3$);
$^1$H-NMR (500 MHz, DMSO-d$_6$) δ 7.28-7.18 (m, 2H), 7.05-6.96 (m, 2H), 4.91 (dd, J=13.1, 4.6 Hz, 1H), 4.83 (dd, J=13.1, 9.5 Hz, 1H), 4.30-4.15 (m, 3H), 4.03 (q, J=7.0 Hz, 2H), 3.78 (d, J=9.2 Hz, 1H), 1.27 (t, J=7.2 Hz, 3H), 1.08 (t, J=7.0 Hz, 3H) ppm;
$^{13}$C-NMR (126 MHz, DMSO-d$_6$) δ 167.4, 166.8, 163.6, 161.6, 132.02, 131.99, 129.9, 129.8, 116.0, 115.9, 77.6, 62.2, 61.9, 54.9, 42.2, 13.9, 13.7 ppm;
IR (CHCl$_3$) ν 3031, 2987, 1733, 1558 cm$^{-1}$;
MS (EI$^+$) 327 (M$^+$), 207 (100);
Elemental analysis
Calculated (for C$_{15}$H$_{18}$FNO$_6$): C, 55.04; H, 5.54; N, 4.28; F, 5.80.
Found: C, 55.24; H, 5.46; N, 4.15; F, 5.67.

Example 17 ethyl 2-ethoxycarbonyl-3-(1-naphthyl)-4-nitrobutyrate

In the same manner as in Example 6A except that trans-1-(2-nitrovinyl)naphthalene was used instead of trans-β-nitrostyrene, the title compound was obtained as a colorless oil. The yield and optical purity are shown in Table 3. The absolute configuration of the obtained compound was not identified.

HPLC analysis conditions:
column: CHIRALCEL OD (manufactured by DAICEL CHEMICAL INDUSTRIES, LTD.),
mobile phase: n-hexane/2-propanol=90/10,
flow rate: 1.0 ml/min,
detection: λ=254 nm,
retention time: isomer (main peak); 14.6 min, isomer; 16.7 min.
$[\alpha]_D^{32}$ +1.60 (c 1.14, CHCl$_3$);
$^1$H-NMR (500 MHz, DMSO-d$_6$) δ 8.19 (d, J=8.6 Hz, 1H), 7.87 (d, J=7.9 Hz, 1H), 7.79 (d, J=7.3 Hz, 1H), 7.65-7.56 (m, 1H), 7.52 (t, J=7.5 Hz, 1H), 7.47-7.34 (m, 2H), 5.29-5.18 (m, 1H), 5.18-5.10 (m, 1H), 5.06 (dd, J=4.7, 13.3 Hz, 1H), 4.28-4.12 (m, 2H), 4.07 (d, J=8.6 Hz, 1H), 4.01-3.88 (m, 2H), 1.23 (t, J=7.2 Hz, 3H), 0.93 (t, J=7.0 Hz, 3H) ppm;
$^{13}$C-NMR (126 MHz, DMSO-d$_6$) δ 167.7, 167.0, 134.1, 132.4, 131.1, 129.2, 128.9, 127.0, 126.1, 125.1, 124.3, 122.4, 77.0, 62.0, 61.9, 54.7, 36.7, 13.8, 13.5 ppm;
IR (CHCl$_3$) ν 3025, 2987, 1732, 1557 cm$^1$;
MS (EI$^+$) 359 (M$^+$), 152 (100);
Elemental analysis
Calculated (for C$_{19}$H$_{21}$NO$_6$): C, 63.50; H, 5.89; N, 3.90.
Found: C, 63.58; H, 5.96; N, 3.76.

Example 18 ethyl 2-ethoxycarbonyl-4-nitro-3-(2-thienyl)butyrate

In the same manner as in Example 6A except that the reaction time was set to 48 hr and trans-2-(2-nitrovinyl)thiophene was used instead of trans-β-nitrostyrene, the title compound was obtained as a colorless oil. The yield and optical purity are shown in Table 3. The absolute configuration of the obtained compound was not identified. HPLC analysis conditions:
column: CHIRALCEL AD (manufactured by DAICEL CHEMICAL INDUSTRIES, LTD.),
mobile phase: n-hexane/2-propanol=90/10,
flow rate: 1.0 ml/min,
detection: λ=254 nm,
retention time: isomer (main peak); 12.0 min, isomer; 21.9 min.
$[\alpha]_D^{32}$ +4.28 (c 0.90, CHCl$_3$);
$^1$H-NMR (500 MHz, DMSO-d$_{16}$) δ 7.22 (d, J=4.9 Hz, 1H), 7.01-6.85 (m, 2H), 5.01-4.81 (m, 2H), 4.62-4.47 (m, 1H), 4.30-4.16 (m, 2H), 4.12 (q, J=7.1 Hz, 2H), 3.87 (d, J=8.2 Hz, 1H), 1.27 (t, J=7.2 Hz, 3H), 1.15 (t, J=7.2 Hz, 3H) ppm;
$^{13}$C-NMR (126 MHz, DMSO-d$_6$) δ 167.3, 166.8, 138.6, 127.0, 126.8, 125.6, 78.0, 62.2, 62.1, 55.5, 38.3, 13.9, 13.7 ppm;
IR (CHCl$_3$) ν 3031, 2988, 1733, 1558 cm$^{-1}$;
MS (EI$^+$) 315 (M$^+$), 195 (100);
Elemental analysis
Calculated (for C$_{13}$H$_{17}$NO$_6$S): C, 49.51; H, 5.43; N, 4.44.
Found: C, 49.67; H, 5.43; N, 4.23.

Example 19 ethyl (S)-2-ethoxycarbonyl-3-(nitromethyl)octanoate

In the same manner as in Example 6A except that the reaction time was set to 48 hr and trans-1-nitro-1-heptene was used instead of trans-β-nitrostyrene, the title compound was obtained as a colorless oil. The yield and optical purity are shown in Table 3.

HPLC analysis conditions:
column: CHIRALCEL OD (manufactured by DAICEL CHEMICAL INDUSTRIES, LTD.),
mobile phase: n-hexane/2-propanol=98/2,
flow rate: 0.5 ml/min,
detection: λ=210 nm,
retention time: (S)-isomer (main peak); 12.7 min, (R)-isomer; 16.3 min.
$[\alpha]_D^{30}$ −4.87 (c 1.00, CHCl$_3$);
$^1$H-NMR (500 MHz, DMSO-d$_6$) δ 4.71 (dd, J=13.4, 4.9 Hz, 1H), 4.54 (dd, J=13.3, 6.9 Hz, 1H), 4.30-4.10 (m, 4H), 3.63 (d, J=5.8 Hz, 1H), 3.02-2.76 (m, 1H), 1.51-1.42 (m, 2H), 1.53-1.19 (m, 12H), 0.88 (t, J=6.9 Hz, 3H) ppm;
$^{13}$C-NMR (126 MHz, DMSO-d$_6$) δ 168.1, 167.9, 76.7, 61.9, 61.7, 52.6, 36.9, 31.4, 29.9, 26.2, 22.3, 14.0, 13.9, 13.8 ppm;
IR (CHCl$_3$) ν 3030, 2960, 2932, 2865, 1730, 1553 cm$^{-1}$;
MS (FAB$^+$) 304 (MH$^+$, 100);
HRMS (FAB$^+$)

Calculated (for [C$_{14}$H$_{26}$NO$_6$]$^+$): 304.1760.
Found: 304.1762.

Example 20 ethyl (S)-2-ethoxycarbonyl-5-methyl-3-(nitromethyl) hexanoate

In the same manner as in Example 6A except that the reaction time was set to 48 hr and trans-4-methyl-1-nitro-1-pentene was used instead of trans-β-nitrostyrene, the title compound was obtained as a colorless oil. The yield and optical purity are shown in Table 3.

HPLC analysis conditions:
column: CHIRALCEL OD (manufactured by DAICEL CHEMICAL INDUSTRIES, LTD.),
mobile phase: n-hexane/2-propanol=98/2,
flow rate: 0.5 ml/min,
detection: λ=210 nm,
retention time: (R)-isomer; 12.1 min, (S)-isomer (main peak); 16.2 min.
[α]$_D^{24}$ −6.92 (c 1.04, CHCl$_3$)
$^1$H-NMR (500 MHz, DMSO-d$_6$) δ 4.71 (dd, J=13.3, 5.0 Hz, 1H), 4.53 (dd, J=13.3, 6.6 Hz, 1H), 4.31-4.14 (m, 4H), 3.62 (d, J=5.5 Hz, 1H), 3.07-2.82 (m, 1H), 1.73-1.57 (m, 1H), 1.36-1.25 (m, 8H), 0.95-0.89 (m, 6H) ppm;
$^{13}$C-NMR (126 MHz, DMSO-d$_6$) δ 168.0, 167.9, 76.8, 61.8, 61.7, 52.6, 38.9, 34.8, 25.0, 22.3, 22.1, 13.93, 13.90 ppm;
IR (CHCl$_3$) ν 3030, 2962, 2873, 1730, 1553 cm$^{-1}$;
MS (EI$^+$) 290 (MH$^+$), 160 (100);
Elemental analysis
Calculated (for C$_{13}$H$_{23}$NO$_6$): C, 53.97; H, 8.01; N, 4.84.
Found: C, 54.20; H, 7.95; N, 4.85.

TABLE 3

| | compound (II) | | | reaction time | yield | optical purity |
|---|---|---|---|---|---|---|
| Example | EWG | R$^8$ | R$^{10}$ | R$^9$ | (hr) | (%) | (% ee) |
| 6A | NO$_2$ | H | H | Ph | 24 | 86 | 93 |
| 15 | NO$_2$ | H | H | 2,6-(OMe)$_2$Ph | 72 | 87 | 93 |
| 16 | NO$_2$ | H | H | 4-F-Ph | 12 | 87 | 92 |
| 17 | NO$_2$ | H | H | 1-naphthyl | 24 | 95 | 92[1] |
| 18 | NO$_2$ | H | H | 2-thienyl | 48 | 74 | 90[1] |
| 19 | NO$_2$ | H | H | n-pentyl | 48 | 78 | 81 |
| 20 | NO$_2$ | H | H | isobutyl | 48 | 88 | 81 |

[1] absolute configuration: not identified

Example 21 methyl 2-methoxycarbonyl-2-methyl-4-nitro-3-phenylbutyrate

In the same manner as in Example 6A except that the reaction time was set to 36 hr and dimethyl methylmalonate was used instead of diethyl malonate, the title compound was obtained as colorless crystals (yield 82%, optical purity 93% ee). melting point: 130-132° C. (n-hexane/ethyl acetate). The absolute configuration of the obtained compound was not identified.

HPLC analysis conditions:
column: CHIRALCEL OD (manufactured by DAICEL CHEMICAL INDUSTRIES, LTD.),
mobile phase: n-hexane/2-propanol=90/10,
flow rate: 1.0 ml/min,
detection: λ=254 nm,
retention time: (R)-isomer; 8.9 min, (S)-isomer (main peak); 13.9 min.
[α]$_D^{32}$ +32.3 (c 1.06, CHCl$_3$);
$^1$H-NMR (500 MHz, DMSO-d$_6$) δ 7.39-7.23 (m, 3H), 7.21-7.09 (m, 2H), 5.12-4.95 (m, 2H), 4.18 (dd, J=9.9, 4.4 Hz, 1H), 3.77 (s, 3H), 3.73 (s, 3H), 1.35 (s, 3H) ppm;
$^{13}$C-NMR (126 MHz, DMSO-d$_6$) δ 171.4, 170.8, 135.0, 129.0, 128.8, 128.5, 77.5, 56.7, 53.0, 52.8, 48.3, 20.2 ppm;
IR (CHCl$_3$) ν 3032, 2955, 1735, 1557 cm$^{-1}$;
MS (EI$^+$) 295 (M$^+$), 189 (100);
MS (FAB$^+$) 310 (MH$^+$, 100);
Elemental analysis
Calculated (for C$_{14}$H$_{17}$NO$_6$): C, 56.94; H, 5.80; N, 4.74.
Found: C, 56.92; H, 5.82; N, 4.64.

Example 22 ethyl (S)-2-ethoxycarbonyl-4-nitro-3-phenylbutyrate (without solvent)

To a mixture of trans-β-nitrostyrene (149 mg, 1.0 mmol) and diethyl malonate (0.304 ml, 2.0 mmol) was added, as an asymmetric catalyst, (R,R)-trans-1-[3,5-bis(trifluoromethyl) phenyl]-3-[2-(N,N-dimethylamino)cyclohexyl]thiourea (20.7 mg, 0.05 mmol), obtained in Example 1A at room temperature under an argon atmosphere. After 12 hr, the reaction mixture was purified by preparative TLC (elution solvent: n-hexane/diethyl ether) to give the title compound as colorless needle crystals (257 mg, yield 83%, optical purity 88%).

Example 23 methyl (R)-2-methoxy-2-methoxycarbonyl-4-nitro-3-phenylbutyrate

In the same manner as in Example 6A except that dimethyl methoxymalonate was used instead of diethyl malonate, the title compound was obtained as a colorless oil. The yield and optical purity are shown in Table 4.

HPLC analysis conditions:
column: CHIRALCEL OD (manufactured by DAICEL CHEMICAL INDUSTRIES, LTD.),
mobile phase: n-hexane/2-propanol=90/10,
flow rate: 0.5 ml/min,
detection: λ=210 nm,
retention time: (R)-isomer (main peak); 16.3 min, (S)-isomer; 21.0 min.
[α]$_D^{28}$ −4.69 (c 1.13, CHCl$_3$);
$^1$H-NMR (500 MHz, CDCl$_3$) δ 7.35-7.18 (m, 5H), 5.24 (dd, J=13.7, 3.4 Hz, 2H), 4.84 (dd, J=10.1, 13.7 Hz, 1H), 4.28 (dd, J=9.9, 3.5 Hz, 1H), 3.83 (S, 3H), 3.58 (S, 3H), 3.46 (S, 3H) ppm;
$^{13}$C-NMR (126 MHz, DMSO-d$_6$) δ 168.0, 167.4, 135.1, 129.4, 128.5, 128.4, 86.0, 76.8, 56.0, 52.9, 52.2, 48.8 ppm;
IR (CHCl$_3$) ν 3032, 2954, 1742, 1556 cm$^{-1}$;
MS (FAB$^+$) 311 (MH$^+$), 104 (100);
Elemental analysis Calculated (for $C_{14}H_{17}NO_7$): C, 54.02; H, 5.50; N, 4.50.
Found: C, 54.18; H, 5.49; N, 4.43.

Example 24 methyl (R)-2-tert-butoxycarbonylamino-2-methoxy-carbonyl-4-nitro-3-phenylbutyrate In the same manner as in Example 6A except that dimethyl tert-butoxycarbonylaminomalonate was used instead of diethyl malonate, the title compound was obtained as a colorless oil. The yield and optical purity are shown in Table 4.

HPLC analysis conditions:
column: CHIRALCEL AD (manufactured by DAICEL CHEMICAL INDUSTRIES, LTD.),
mobile phase: n-hexane/2-propanol=90/10,
flow rate: 1.0 ml/min,
detection: λ=210 nm,
retention time: (R)-isomer (main peak); 11.5 min, (S)-isomer; 17.5 min.
$[\alpha]_D^{24}$+27.1 (c 0.94, CHCl$_3$);
$^1$H-NMR (500 MHz, CDCl$_3$) δ 7.36-7.17 (m, 5H), 5.94 (s, 1H), 5.50 (dd, J=13.1, 2.4 Hz, 1H), 4.72 (t, J=12.5 Hz, 1H), 4.62 (dd, J=11.9, 2.8 Hz, 1H), 4.34-4.21 (m, 2H), 4.19-4.09 (m, 1H), 4.05-3.95 (m, 1H), 1.46 (s, 9H), 1.29 (t, J=7.2 Hz, 3H), 1.19 (t, J=7.2 Hz, 3H) ppm;
$^{13}$C-NMR (126 MHz, DMSO-d$_6$) δ 166.4, 166.3, 154.8, 134.1, 129.0, 128.7, 128.7, 81.2, 77.0, 67.5, 63.4, 62.7, 48.2, 28.1, 13.8, 13.7 ppm;
IR (CHCl$_3$) ν 3396, 3027, 2985, 1743, 1715, 1555, 1485 cm$^{-1}$;
MS (FAB$^+$) 425 (MH$^+$), 325(100);
HRMS (FAB$^+$)
Calculated (for [$C_{20}H_{29}N_2O_8$]$^+$): 424.1846.
Found: 425.1932.

Example 25 methyl (R)-2-chloro-2-methoxycarbonyl-4-nitro-3-phenylbutyrate

In the same manner as in Example 6A except that dimethyl chloromalonate was used instead of diethyl malonate, the title compound was obtained as colorless needle crystals. The yield and optical purity are shown in Table 4. melting point: 175-177° C. (n-hexane/ethyl acetate).

HPLC analysis conditions:
column: CHIRALCEL OD (manufactured by DAICEL CHEMICAL INDUSTRIES, LTD.),
mobile phase: n-hexane/2-propanol=90/10,
flow rate: 0.5 ml/min,
detection: λ=210 nm,
retention time: (R)-isomer (main peak); 18.6 min, (S)-isomer; 23.3 min.
$[\alpha]_D^{20}$-6.16 (c 0.85, CHCl$_3$);
$^1$H-NMR (500 MHz, CDCl$_3$) δ 7.42-7.25 (m, 3H), 5.21 (dd, J=13.4, 3.3 Hz, 1H), 5.00 (dd, J=13.4, 10.4 Hz, 1H), 4.63 (dd, J=10.5, 3.2 Hz, 1H), 3.84 (s, 3H), 3.59 (s, 3H) ppm;
$^{13}$C-NMR (126 MHz, DMSO-d$_6$) δ 165.7, 164.5, 133.3, 129.4, 129.0, 128.6, 76.6, 72.3, 54.6, 54.3, 48.2 ppm;
IR (CHCl$_3$) ν 3029, 2957, 1750, 1560 cm$^{-1}$;
MS (FAB$^+$) 316 (MH$^+$), 154(100);
Elemental analysis
Calculated (for $C_{13}H_{14}ClNO_6$): C, 49.46; H, 4.47; N, 4.44.
Found: C, 49.46; H, 4.44; N, 4.41.

Example 26 methyl 2-(2'-nitro-1'-phenylethyl)-1-oxo-1,2,3,4-tetrahydronaphthalene-2-carboxylate In the same manner as in Example 6A except that methyl 1-oxo-1,2,3,4-tetrahydronaphthalene-2-carboxylate was used instead of diethyl malonate, the title compound (diastereomer mixture) (90% d.e., optical purity of the main diastereomer: 90% e.e., yield 97%) was obtained. The obtained diastereomer mixture was recrystallized from n-hexane/ethyl acetate to give the main diastereomer of the title compound as colorless plate crystals. The yield and optical purity are shown in Table 4. melting point: 101-103° C. (n-hexane/ethyl acetate). The absolute configuration of the obtained compound was not identified.

HPLC analysis conditions:
column: CHIRALCEL OD (manufactured by DAICEL CHEMICAL INDUSTRIES, LTD.),
mobile phase: n-hexane/2-propanol=90/10,
flow rate: 0.5 ml/min,
detection: λ=254 nm,
retention time: isomer (main peak); 27.9 min, isomer; 46.7 min.
$[\alpha]_D^{20}$+51.0 (c 0.75, CHCl$_3$);
$^1$H-NMR (500 MHz, CDCl$_3$) δ 8.03 (d, J=7.9 Hz, 1H), 7.50 (t, J=7.5 Hz, 1H), 7.41-7.23 (m, 6H), 7.19 (d, J=7.6 Hz, 1H), 5.15 (dd, J=13.5, 3.5 Hz, 1H), 5.05 (dd, J=13.5, 10.5 Hz, 1H), 4.20 (dd, J=10.5, 3.5 Hz, 1H), 3.65 (s, 3H), 3.05-2.89 (m, 2H), 2.47-2.39 (m, 1H), 2.10-1.98 (m, 1H) ppm;
$^{13}$C-NMR (126 MHz, DMSO-d$_6$) δ 194.3, 170.3, 142.5, 135.9, 134.1, 131.6, 129.9, 128.8, 128.7, 128.5, 128.3, 127.1, 77.8, 59.7, 52.7, 47.1, 30.7, 25.5 ppm;
IR (CHCl$_3$) ν 3031, 2954, 1736, 1687, 1601 cm$^{-1}$;
MS (FAB$^+$) 354 (MH$^+$), 189 (100);
Elemental analysis
Calculated (for $C_{20}H_{19}ClNO_5$): C, 67.98; H, 5.42; N, 3.96.
Found: C, 67.79; H, 5.43; N, 3.95.

TABLE 4

| | nucleophilic reagent (III) | | yield | optical purity |
|---|---|---|---|---|
| Example | | $R^{16}$ | (%) | (% ee) |
| 23 | MeO$_2$C–C($R^{16}$)–CO$_2$Me | OMe | 89 | 94 |
| 24 | | NHCO$_2$t-Bu | 81 | 82 |
| 25 | | Cl | 100 | 99[1)] |
| 26 | 2-oxo-1,2,3,4-tetrahydronaphthalene-CO$_2$Me | | 97[2)] | 90[3)4)] |

[1)]after recrystallization
[2)]diastereomer mixture (90% d.e.)
[3)]main diastereomer
[4)]absolute configuration: not identified

INDUSTRIAL APPLICABILITY

According to the present invention, a novel asymmetric urea compound (I), which is a non-metallic asymmetric catalyst enabling an asymmetric conjugate addition reaction in a high yield and with high stereoselectivity, is provided, and using this compound for an asymmetric conjugate addition reaction, an advantageous production method of an asymmetric compound [asymmetric compound (IV)] is provided.

Since the asymmetric urea compound (I) of the present invention is non-metallic and does not require treatments of metal waste liquid and the like, it is an environmentally-friendly catalyst. Moreover, since it is non-metallic, the compound can be recovered and reused easily.

Since the production method of the present invention is applicable to bulky nucleophilic reagents such as tertiary carbon and the like, the method permits a broad range of application.

Furthermore, since the reaction conditions are mild and the method can also be performed without solvent, it is a highly practical method.

This application is based on patent application Nos. 2003-189096 and 2003-421688 filed in Japan, the contents of which are hereby incorporated by reference.

The invention claimed is:

1. A compound represented by the formula (I):

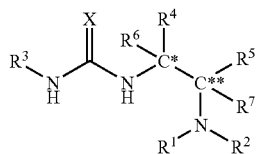

(I)

wherein
X is a sulfur atom;
C* and C** are each independently an asymmetric carbon;
$R^1$ and $R^2$ are
the same or different and each is methyl, ethyl or isopropyl, or form isoindoline together with the nitrogen atom they are bonded to;
R3 is
a lower alkyl group optionally having substituent(s), an aralkyl group optionally having substituent(s), an aryl group optionally having substituent(s) or a heteroaryl group optionally having substituent(s);
$R^4$ and $R^5$ are
the same or different and each is a lower alkyl group optionally having substituent(s), an aralkyl group optionally having substituent(s) or an aryl group optionally having substituent(s), or $R^4$ and $R^5$ form, together with the asymmetric carbons they are respectively bonded to, a homocyclic ring optionally having substituent(s) or a heterocycle optionally having substituent(s); and
$R^6$ and $R^7$ are
the same or different and each is a hydrogen atom or a lower alkyl group optionally having substituent(s),
or a salt thereof.

2. The compound of claim 1, wherein $R^4$ and $R^5$ form a $C_{3-7}$ cycloalkane together with the asymmetric carbons they are respectively bonded to.

3. (R,R)-trans-1-[3,5-bis(trifluoromethyl)phenyl]-3-[2-(N,N-dimethylamino)cyclohexyl]thiourea.

4. The compound of claim 1, wherein $R^4$ and $R^5$ form, together with the asymmetric carbons they are respectively bonded to, a homocyclic ring optionally having substituent(s) or a heterocycle optionally having substituent(s).

5. The compound of claim 4, wherein $R^4$ and $R^5$ form, together with the asymmetric carbons they are respectively bonded to, cyclopropane, cyclobutane, cyclopentane or cyclohexane.

6. The compound of claim 5, wherein $R^4$ and $R^5$ form cyclohexane together with the asymmetric carbons they are respectively bonded to, and $R^6$ and $R^7$ are each a hydrogen atom.

7. The compound of claim 6, wherein the absolute configurations of C* and C** are both S-configurations or both R-configurations.

* * * * *